US009951384B2

(12) United States Patent
Schnable et al.

(10) Patent No.: US 9,951,384 B2
(45) Date of Patent: Apr. 24, 2018

(54) GENOTYPING BY NEXT-GENERATION SEQUENCING

(71) Applicant: Data2Bio, Ames, IA (US)

(72) Inventors: Patrick S. Schnable, Ames, IA (US); Sanzhen Liu, Ames, IA (US); Wei Wu, Johnston, IA (US)

(73) Assignee: DATA2BIO, Ames, IA (US)

( * ) Notice: Subject to any disclaimer, the term of this patent is extended or adjusted under 35 U.S.C. 154(b) by 124 days.

(21) Appl. No.: 14/723,678

(22) Filed: May 28, 2015

(65) Prior Publication Data

US 2015/0344947 A1 Dec. 3, 2015

Related U.S. Application Data

(63) Continuation of application No. 13/739,874, filed on Jan. 11, 2013, now abandoned.

(60) Provisional application No. 61/586,596, filed on Jan. 13, 2012.

(51) Int. Cl.
*C12Q 1/68* (2018.01)
*C12N 15/10* (2006.01)

(52) U.S. Cl.
CPC ....... *C12Q 1/6874* (2013.01); *C12N 15/1065* (2013.01); *C12Q 1/683* (2013.01); *C12Q 1/6806* (2013.01); *C12Q 1/6869* (2013.01)

(58) Field of Classification Search
None
See application file for complete search history.

(56) References Cited

U.S. PATENT DOCUMENTS

| 4,863,849 | A | 9/1989 | Melamede |
| 5,695,934 | A | 12/1997 | Brenner et al. |
| 5,714,330 | A | 2/1998 | Brenner et al. |
| 5,750,341 | A | 5/1998 | Macevicz et al. |
| 5,912,148 | A | 6/1999 | Eggerding et al. |
| 5,935,793 | A | 8/1999 | Wong |
| 6,130,073 | A | 10/2000 | Eggerding |
| 6,210,891 | B1 | 4/2001 | Skarpnack et al. |
| 6,258,568 | B1 | 7/2001 | Skarpnack et al. |
| 6,274,320 | B1 | 8/2001 | Rothberg et al. |
| 6,306,597 | B1 | 10/2001 | Macevicz et al. |
| 6,432,360 | B1 | 8/2002 | Church et al. |
| 6,472,185 | B2 | 10/2002 | McCaskey-Feazel et al. |
| 6,485,944 | B1 | 11/2002 | Church et al. |
| 6,511,803 | B1 | 1/2003 | Church et al. |
| 6,787,308 | B2 | 9/2004 | Balasubramanian et al. |
| 6,818,395 | B1 | 11/2004 | Quake et al. |
| 6,825,010 | B2 | 11/2004 | Spier et al. |
| 6,833,246 | B2 | 12/2004 | Balasubramanian et al. |
| 6,911,345 | B2 | 6/2005 | Quake et al. |
| 6,913,879 | B1 | 7/2005 | Schena et al. |
| 6,958,225 | B2 | 10/2005 | Dong |
| 6,969,488 | B2 | 11/2005 | Bridgham et al. |
| 7,115,400 | B1 | 10/2006 | Adessi et al. |
| 7,169,560 | B2 | 1/2007 | Lapidus et al. |
| 7,170,050 | B2 | 1/2007 | Turner et al. |
| 7,282,337 | B1 | 10/2007 | Harris et al. |
| 7,302,146 | B2 | 11/2007 | Turner et al. |
| 7,313,308 | B2 | 12/2007 | Turner et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 7,476,503 | B2 | 1/2009 | Turner et al. |
| 7,482,120 | B2 | 1/2009 | Buzby |
| 7,501,245 | B2 | 3/2009 | Quake |
| 7,510,829 | B2 | 3/2009 | Faham et al. |
| 8,481,257 | B2 | 7/2013 | van Eijk et al. |
| 8,685,889 | B2 | 4/2014 | van Eijk et al. |
| 8,785,353 | B2 | 7/2014 | van Eijk et al. |
| 8,815,512 | B2 | 8/2014 | van Eijk et al. |
| 8,911,945 | B2 | 12/2014 | van Eijk et al. |
| 2003/0082572 | A1 | 5/2003 | Spier et al. |
| 2003/0096239 | A1 | 5/2003 | Gunderson et al. |
| 2003/0096291 | A1 | 5/2003 | Faham et al. |
| 2004/0081996 | A1 | 4/2004 | Landers et al. |
| 2004/0132056 | A1 | 7/2004 | Su et al. |
| 2004/0185484 | A1 | 9/2004 | Costa et al. |
| 2004/0259105 | A1 | 12/2004 | Fan et al. |
| 2005/0130173 | A1 | 6/2005 | Leamon et al. |
| 2006/0063158 | A1 | 3/2006 | Dong et al. |
| 2006/0121461 | A1* | 6/2006 | Harms ............... C12N 15/1034 435/6.14 |
| 2007/0036511 | A1 | 2/2007 | Lundquist et al. |
| 2007/0072196 | A1 | 3/2007 | Xu et al. |
| 2007/0077564 | A1 | 4/2007 | Roitman et al. |

(Continued)

FOREIGN PATENT DOCUMENTS

EP 0534858 A1 3/1993
EP 0534858 B1 4/2000

(Continued)

OTHER PUBLICATIONS

Liu et al. (DLA-Based Strategies for Cloning Insertion Mutants: Cloning the gl4 Locus of Maize Using Mu Transposon Tagged Alleles, Genetics 183: 1215-1225 (Dec. 2009)).*
Rogers et al. (Closing bacterial genomic sequence gaps with adaptor-PCR, BioTechniques 39:31-34 (Jul. 2005).*
Davies et al., A Novel Integrative Conjugative Element Mediates Genetic Transfer from Group G *Streptococcus* to Other β-Hemolytic Streptococci, Journal of Bacteriology, Apr. 2009, p. 2257-2265).*
Ahmed et al. (Identification of genetic differences between two Campylobacter jejuni strains with different colonization potentials, Microbiology (2002), 148, 1203-1212).*
Davey et al. (Genome-wide genetic marker discovery and genotyping using next-generation sequencing, Nature Reviews Genetics, vol. 12, Jul. 2011, pp. 499-510).*
Elshire et al. (A Robust, Simple Genotyping-by-Sequencing (GBS) Approach for High Diversity Species, PLoS One, vol. 6, issue 5, e19379, May 2011).*

(Continued)

*Primary Examiner* — Aaron A Priest
(74) *Attorney, Agent, or Firm* — Casimir Jones, S.C.

(57) ABSTRACT

Provided herein is technology relating to genotyping and particularly, but not exclusively, to methods for genotyping one or more organisms by genome sequencing.

16 Claims, 4 Drawing Sheets

(56) References Cited

U.S. PATENT DOCUMENTS

| | | |
|---|---|---|
| 2007/0128133 A1 | 6/2007 | Eid et al. |
| 2007/0134128 A1 | 6/2007 | Korlach et al. |
| 2007/0141598 A1 | 6/2007 | Turner et al. |
| 2007/0161017 A1 | 7/2007 | Eid et al. |
| 2007/0188750 A1 | 8/2007 | Lundquist et al. |
| 2007/0196846 A1 | 8/2007 | Hanzel et al. |
| 2007/0206187 A1 | 9/2007 | Lundquist et al. |
| 2007/0231804 A1 | 10/2007 | Korlach et al. |
| 2007/0238679 A1 | 10/2007 | Rank et al. |
| 2007/0250274 A1 | 10/2007 | Volkov et al. |
| 2008/0003007 A1 | 1/2008 | Jang et al. |
| 2008/0030628 A1 | 2/2008 | Lundquist et al. |
| 2008/0032301 A1 | 2/2008 | Rank et al. |
| 2008/0050747 A1 | 2/2008 | Korlach et al. |
| 2008/0080059 A1 | 4/2008 | Dixon et al. |
| 2008/0095488 A1 | 4/2008 | Foquet et al. |
| 2008/0108082 A1 | 5/2008 | Rank et al. |
| 2008/0128627 A1 | 6/2008 | Lundquist et al. |
| 2008/0145278 A1 | 6/2008 | Korlach et al. |
| 2008/0152280 A1 | 6/2008 | Lundquist et al. |
| 2008/0152281 A1 | 6/2008 | Lundquist et al. |
| 2008/0153095 A1 | 6/2008 | Williams et al. |
| 2008/0153100 A1 | 6/2008 | Rank et al. |
| 2008/0157005 A1 | 7/2008 | Lundquist et al. |
| 2008/0160531 A1 | 7/2008 | Korlach et al. |
| 2008/0165346 A1 | 7/2008 | Lundquist et al. |
| 2008/0176241 A1 | 7/2008 | Eid et al. |
| 2008/0176316 A1 | 7/2008 | Eid et al. |
| 2008/0176769 A1 | 7/2008 | Rank et al. |
| 2008/0199874 A1 | 8/2008 | Otto et al. |
| 2008/0199932 A1 | 8/2008 | Hanzel et al. |
| 2008/0206764 A1 | 8/2008 | Williams et al. |
| 2008/0212960 A1 | 9/2008 | Lundquist et al. |
| 2008/0241951 A1 | 10/2008 | Battulga et al. |
| 2009/0026082 A1 | 1/2009 | Rothberg et al. |
| 2009/0035777 A1 | 2/2009 | Kokoris et al. |
| 2009/0127589 A1 | 5/2009 | Rothberg et al. |
| 2009/0253581 A1* | 10/2009 | Van Eijk ............. C12Q 1/6853 506/2 |
| 2009/0269749 A1* | 10/2009 | Van Eijk ............. C12Q 1/6827 435/6.11 |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0301398 A1 | 12/2010 | Rothberg et al. |
| 2010/0304990 A1 | 12/2010 | Gifford et al. |
| 2012/0196279 A1* | 8/2012 | Underwood ............ C12P 19/34 435/6.1 |
| 2014/0274744 A1 | 9/2014 | van Eijk et al. |
| 2014/0295428 A1 | 10/2014 | van Eijk et al. |
| 2014/0315728 A1 | 10/2014 | van Eijk et al. |

FOREIGN PATENT DOCUMENTS

| | | |
|---|---|---|
| WO | 1998044151 | 10/1998 |
| WO | 2000018957 | 4/2000 |
| WO | 2000024939 | 5/2000 |
| WO | 2000063437 | 10/2000 |
| WO | 2001007664 A2 | 2/2001 |
| WO | 2002022869 | 3/2002 |
| WO | 2002077287 | 10/2002 |
| WO | 2003004690 | 1/2003 |
| WO | 2003012118 | 2/2003 |
| WO | 2003012118 A1 | 2/2003 |
| WO | 2003054142 | 7/2003 |
| WO | 2004022758 | 3/2004 |
| WO | 2004069849 | 8/2004 |
| WO | 2004070005 | 8/2004 |
| WO | 2004070007 | 8/2004 |
| WO | 2005003375 | 1/2005 |
| WO | 2006084132 | 10/2006 |
| WO | 2006137733 | 12/2006 |
| WO | 2007073165 A1 | 6/2007 |
| WO | 2007114693 A2 | 10/2007 |
| WO | 2008045575 A2 | 4/2008 |
| WO | 2010128091 A1 | 11/2010 |

OTHER PUBLICATIONS

Baird et al. (Rapid SNP Discovery and Genetic Mapping Using Sequenced RAD Markers, PLoS One, vol. 3, issue 10, e3376, Oct. 2008).*

Knapp et al. (Next Generation Sequencing of Ancient DNA: Requirements, Strategies and Perspectives, Genes (Basel). Sep. 2010; 1(2): 227-243. Published online Jul. 28, 2010).*

Meyer et al. (Parallel tagged sequencing on the 454 platform, Nat Protoc. 2008;3(2):267-78, Published online: Jan. 31, 2008).*

Smith et al. (Highly-multiplexed barcode sequencing: an efficient method for parallel analysis of pooled samples, Nucleic Acids Res. Jul. 2010;38(13):e142. doi: 10.1093/nar/gkq368. Epub May 11, 2010).*

Andalfatto et al. (Multiplexed shotgun genotyping for rapid and efficient genetic mapping, Genome Res. 2011 21: 610-617 originally published online Jan. 13, 2011).*

Deena1 Bioinformatics Jul. 16, 2011.*

Deena2 Bioinformatics Jul. 16, 2011.*

Etter et al., "SNP discovery and genotyping for evolutionary genetics using RAD sequencing." Methods Mol Biol. 2011;772:157-78.

Frank et al., "BARCRAWL and BARTAB: software tools for the design and implementation of barcoded primers for highly multiplexed DNA sequencing." BMC Bioinformatics. Oct. 29, 2009;10:362.

Hajibabaei et al., "Design and applicability of DNA arrays and DNA barcodes in biodiversity monitoring." BMC Biol. Jun. 13, 2007;5:24.

Parameswaran et al., "A pyrosequencing-tailored nucleotide barcode design unveils opportunities for large-scale sample multiplexing." Nucleic Acids Res. 2007;35(19):e130.

Xu et al., Design of 240,000 orthogonal 25mer DNA barcode probes. Proc Natl Acad Sci U S A. Feb. 17, 2009;106 (7):2289-94.

Meyer et al., "Parallel tagged sequencing on the 454 platform." Nat Protoc. 2008;3(2):267-78.

Islam et al., "Detection, Validation, and Application of Genotyping-by-Sequencing Based Single Nucleotide Polymorphisms in Upland Cotton" The Plant Genome, Mar. 2015, 10 pages.

Examination Report of related EP Application No. 13735665.5, dated Nov. 14, 2016,8 pages.

Adessi et al., "Solid phase DNA amplification: characterisation of primer attachment and amplification mechanisms." Nucleic Acids Res. Oct. 15, 2000; 28(20):E87.

Andolfatto et al., "Multiplexed shotgun genotyping for rapid and efficient genetic mapping." Genome Res. Apr. 2011; 21(4):610-7.

Astier et al., "Toward single molecule DNA sequencing: direct identification of ribonucleoside and deoxyribonucleoside 5'-monophosphates by using an engineered protein nanopore equipped with a molecular adapter." J Am Chem Soc. Feb. 8, 2006; 128(5):1705-10.

Baird et al., "Rapid SNP discovery and genetic mapping using sequenced RAD markers." PLoS One. 2008; 3(10):e3376.

Bennett et al., "Toward the 1,000 dollars human genome." Pharmacogenomics. Jun. 2005; 6(4):373-82.

Brenner et al., "Gene expression analysis by massively parallel signature sequencing (MPSS) on microbead arrays." Nat Biotechnol. Jun. 2000; 18(6):630-4.

Elshire et al., "A robust, simple genotyping-by-sequencing (GBS) approach for high diversity species." PLoS One. May 4, 2011; 6(5):e19379.

Korlach et al. "Selective aluminum passivation for targeted immobilization of single DNA polymerase molecules in zero-mode waveguide nanostructures." Proc Natl Acad Sci U S A. Jan. 29, 2008; 105(4):1176-81.

Lai et al., "Genome-wide patterns of genetic variation among elite maize inbred lines." Nat Genet. Nov. 2010; 42 (11):1027-30.

Liu et al., "DLA-based strategies for cloning insertion mutants: cloning the gl4 locus of maize using Mu transposon tagged alleles." Genetics. Dec. 2009; 183(4):1215-25.

(56) References Cited

OTHER PUBLICATIONS

Maclean et al., "Application of 'next-generation' sequencing technologies to microbial genetics." Nat Rev Microbiol. Apr. 2009; 7(4):287-96.
Magnuson et al., "Substrate nucleotide-determined non-templated addition of adenine by Taq DNA polymerase: implications for PCR-based genotyping and cloning." Biotechniques. Oct. 1996; 21(4):700-9.
Margulies et al., "Genome sequencing in microfabricated high-density picolitre reactors." Nature. Sep. 15, 2005; 437 (7057):376-80.
Mitra et al., "Fluorescent in situ sequencing on polymerase colonies." Anal Biochem. Sep. 1, 2003; 320(1):55-65.
Morozova & Marra, "Applications of next-generation sequencing technologies in functional genomics." Genomics. Nov. 2008; 92(5):255-64.
Pennisi, "Genomics. Semiconductors inspire new sequencing technologies." Science. Mar. 5, 2010; 327(5970):1190.
Shendure et al., "Accurate multiplex polony sequencing of an evolved bacterial genome." Science. Sep. 9, 2005; 309(5741):1728-32.
Voelkerding et al., "Next-generation sequencing: from basic research to diagnostics." Clin Chem. Apr. 2009; 55(4):641-58.
Davey et al., "Genome-wide genetic marker discovery and genotyping using next-generation sequencing." Nature Reviews: Genetics Jul. 2011, 12:499-510.
Deena1 Bioinformatics Jul. 16, 2011.
Definition of Genotype, MedicineNet.com; 2014.
Rogers et al., "Closing bacterial genomic sequence gaps with adaptor-PCR." BioTechniques Jul. 2005, 39:31-34.
Davies et al., "A Novel Integrative Conjugative Element Mediates Genetic Transfer from Group G *Streptococcus* to Other beta-Homolytic Streptococci." Journal of Bacteriology Apr. 2009, 191(7):2257-2265.
Ahmed et al., "Identification of genetic differences between two Campylobacter jejuni strains with different colonization potentials." Microbiology 2002, 148:1203-1212.
AFLP manual 2003.
Altschul et al., "Issues in searching molecular sequence databases." Nat Genet. Feb. 1994;6(2):119-29.
Altshuler et al., "An SNP map of the human genome generated by reduced representation shotgun sequencing." Nature. Sep. 28, 2000;407(6803):513-6.
Bevan et al. "Sequencing of PCR-amplified DNA." PCR Methods Appl. May 1992;1(4):222-8.
Brugmans et al., "A new and versatile method for the successful conversion of AFLP markers into simple single locus markers." Nucleic Acids Res. May 15, 2003;31(10):e55.
Chee "Enzymatic multiplex DNA sequencing." Nucleic Acids Res. Jun. 25, 1991;19(12):3301-5.
Church et al., "Multiplex DNA sequencing." Science. Apr. 8, 1988;240(4849):185-8.
Fu et al., "Types and frequencies of sequencing errors in methyl-filtered and high c0t maize genome survey sequences." Plant Physiol. Aug. 2004;135(4):2040-5.
Holton et al., "A simple and efficient method for direct cloning of PCR products using ddT-tailed vectors." Nucleic Acids Res. Mar. 11, 1991;19(5):1156.
Jordan et al., "Genome complexity reduction for SNP genotyping analysis." Proc Natl Acad Sci U S A. Mar. 5, 2002;99(5):2942-7.
Kennedy et al., "Large-scale genotyping of complex DNA." Nat Biotechnol. Oct. 2003;21(10):1233-7.

Khamis et al., "rpoB gene sequencing for identification of *Corynebacterium* species." J Clin Microbial. Sep. 2004;42(9):3925-31.
THESIS_MANNOCCI_2009_172 pages.
Masiga et al., "Amplified (restriction) fragment length polymorphism (AFLP) analysis." Methods Mol Biol. 2004;270:173-86.
Miner et al., "Molecular barcodes detect redundancy and contamination in hairpin-bisulfite PCR." Nucleic Acids Res. Sep. 30, 2004;32(17):e135.
Nicod et al., "SNPs by AFLP (SBA): a rapid SNP isolation strategy for non-model organisms." Nucleic Acids Res. Mar. 1, 2003;31(5):e19.
Okano et al., "Classified fingerprinting: A method of comprehensive analysis for comparing megabase genomes." Nucleic Acids Res Suppl. 2001;(1):93-4.
Qiu et al., "DNA sequence-based "bar codes" for tracking the origins of expressed sequence tags from a maize cDNA library constructed using multiple mRNA sources" Plant Physiol. Oct. 2003;133(2):475-81.
Sanger et al., "DNA sequencing with chain-terminating inhibitors." Proc Natl Acad Sci U S A. Dec. 1977;74(12):5463-7.
Seo et al., "Photocleavable fluorescent nucleotides for DNA sequencing on a chip constructed by site-specific coupling chemistry." Proc Natl Acad Sci U S A. Apr. 13, 2004;101(15):5488-93.
Syvänen "Toward genome-wide SNP genotyping." Nat Genet. Jun. 2005;37 Suppl:S5-10.
Van Den Braak et al. "A new high-throughput AFLP approach for identification of new genetic polymorphism in the genome of the clonal microorganism *Mycobacterium tuberculosis*." J Microbial Methods. Jan. 2004;56(1):49-62.
Volkmuth et al., "Technical advances: genome-wide cDNA-AFLP analysis of the *Arabidopsis transcriptome*." OMICS. 2003 Summer;7(2):143-59.
Vooijis et al., "Libraries for each human chromosome, constructed from sorter-enriched chromosomes by using inker-adaptor PCR." Am J Hum Genet. Mar. 1993;52(3):586-97.
Vos et al., "AFLP: a new technique for DNA fingerprinting." Nucleic Acids Res. Nov. 11, 1995;23(21):4407-14.
Vysotskaia et al., "Development and characterization of genome-wide single nucleotide polymorphism markers in the green alga *Chlamydomonas reinhardtii*."Plant Physiol. Oct. 2001;127(2):386-9.
Wenzl et al., "Diversity Arrays Technology (DArT) for whole-genome profiling of barley." Proc Natl Arad Sci U S A. Jun. 29, 2004;101(26):9915-20.
Yuanxin et al., "T-linker-specific ligation PCR (T-linker PCR): an advanced PCR technique for chromosome walking or for isolation of tagged DNA ends." Nucleic Acids Res. Jun. 15, 2003;31(12):e68.
Examination Report of related EP Application No. 13735665.5, dated Jan. 24, 2018, 12 pages.
Van Orsouw et al., "Complexity reduction of polymorphic sequences (CRoPS): a novel approach for large-scale polymorphism discovery in complex genomes."PLoS One. Nov. 14, 2007;2(11):e1172.
Liu et al., DLA-Based Strategies for Cloning Insertion Mutants, Genetics 183:1215-1225 (2009), 19 pages.†
Baird et al., Rapid SNP Discovery and Genetic Mapping Using Sequenced RAD Markers, PLoS One 3(10):e3376 (2008), 7 pages.†
Elshire et al., A Robust, Simple Genotyping-by-Sequencing (GBS) Approach for High Diversity Species, PLoS ONE 6(5):e19379 (2011), 10 pages.†

\* cited by examiner
† cited by third party tGBS (tunable GBS)

Step 1: Digestion

NsiI site      BfuCI site
5' RCATGY————————AACAGATC 3'
3' YGTACR————————TTGTCTAG 5'

Double digestions
5'     Y————————AACA 3'
3' GTACR————————TTGTCTAG 5'

Step 2: Ligation      barcode (index)      (p) bfuci12mm

SEQ ID NO. 34 5' ACACGACGCTCTTCCGATCTXXXXXXXXCATGY————————AACAGATCGGAAGAGCTCGT 3' SEQ ID NO. 42
3'      GTACR————————TTGTCTAG      5'

Step 3: Selective PCR
     common1 (20bp)          bfuci3ACAA (20nt)
SEQ ID NO. 26 5' ACACGACGCTCTTCCGATCT 3'      3' TTGTCTAGCCTTCTCGAGCA 5' SEQ ID NO. 43
SEQ ID NO. 37 5' ACACGACGCTCTTCCGATCTXXXXXXXXCATGY————————AACAGATCGGAAGAGCTCGT 3' SEQ ID NO. 42
3'      GTACR————————TTGTCTAG      5'

Step 4: Final PCR
     Illumina primer 1.1 (58bp)          final3 (30bp)
SEQ ID NO. 48 ACACGACGCTCTTCCGATCT 3'      3' TGTCTAGCCTTCTCGAGCA SEQ ID NO. 49
SEQ ID NO. 39 5' ACACGACGCTCTTCCGATCTXXXXXXXXCATGY————————AACAGATCGGAAGAGCTCGT 3' SEQ ID NO. 42

Figure 1

SPG (Single Primer Genotyping)

Step 1: Digestion (NspI as the example)
NspI site
5' RCATGY----------[A/G]-------------------- 3'
3' YGTACR----------[T/C]-------------------- 5'

NspI digestion
5' Y----------[A/G]-------------------- 3'
3' GTACR----------[T/C]-------------------- 5'

Step 2: Ligation with a barcoded/indexed oligo (nspIxx)
5' [Common_seq]]BARCODE]CATGY----------[A/G]-------------------- 3'
3'                     GTACR----------[T/C]-------------------- 5'

Step 3: target PCR with a common primer and a target specific primer (TSP)

5' [Common_seq]]BARCODE]CATGY----------[A/G]-------------------- 3'

Step 4: Final PCR to prepare a NGS library

Illumina primer 1                                    Illumina primer 2

5' [Common_seq]]BARCODE]CATGY----------[A/G]------------======== 3'
3' [Common_seq]]BARCODE]CATGY----------[A/G]------------======== 5'

Figure 2 tGBS-SE-CTA selection

```
              NsiI                        BfuCI
         5' NNNNN---------------------(CTA)GATC 3'
         3' NNNNN---------------------(GAT)CTAG 5'

Double digestions
         5' T---------------------(CTA)        3'
         3' GTACA-------------------(GAT)CTAG 5'

Ligation
                  barcoded asy a-oligo                                    (P) s-SSOI5
SEQ ID NO. 44 5' A*CACGACGCTCTTCCGATCTXXXXXXXXXCATGT---------------(CTA) GATCGGAAGAGCTC*G 3' SEQ ID NO. 29
              3'                          GTAC A---------------------(GAT) CTAG              5'

Selective PCR (15 cycles)
              s-common1 (29bp)                                   s-SSOI6CTA (19nt)
SEQ ID NO. 33 5' A*CACGACGCTCTTCCGATC*T 3'              3' (G*A*T*) CTAGCCTTCTCGAGC A 5' SEQ ID NO. 45
SEQ ID NO. 34 5' A*CACGACGCTCTTCCGATCT XXXXXXXXXCATGT---------------(C T A) GATCGGAAGAGCTCG*T        3' SEQ ID NO. 29

Product of Selective PCR
SEQ ID NO. 34 5' A*CACGACGCTCTTCCGATCTXXXXXXXXXCATGT---------------(C T A) GATCGGAAGAGCTCG  3' SEQ ID NO. 47
SEQ ID NO. 46 3' T GTGCTGCGAGAAGGCTAG AXXXXXXXXXGTACA---------------(G*A*T*) CTAGCCTTCTCGAGCA  5' SEQ ID NO. 45

Final PCR with SE primers' (12 cycles)
         # SE Primers
SEQ ID NO. 31 s-SE-P1  5' A*ATGATACGGCGACCACCGAGATCTACACTCTTTCCCTACACGACGCTCTTCCGATC*T 3'
SEQ ID NO. 32 s-SE-P2AG 5' C*AAGCAGAAGACGGCATACGAGCTCTTCCGATCTA*G 3'
```

Figure 3

SEQUENCE LISTING

<160> NUMBER OF SEQ ID NOS: 41

<210> SEQ ID NO 1
<211> LENGTH: 32

```
<212> TYPE: DNA
<213> ORGANISM: Artificial Sequence
<220> FEATURE:
<223> OTHER INFORMATION: Synthetic

<400> SEQUENCE: 1
acacgacgct cttccgatct cgtatatgca tg                              32

<210> SEQ ID NO 2
<211> LENGTH: 31
<212> TYPE: DNA
<213> ORGANISM: Artificial Sequence
<220> FEATURE:
<223> OTHER INFORMATION: Synthetic

<400> SEQUENCE: 2
acacgacgct cttccgatct cacgctacat g                               31

<210> SEQ ID NO 3
<211> LENGTH: 32
<212> TYPE: DNA
<213> ORGANISM: Artificial Sequence
<220> FEATURE:
<223> OTHER INFORMATION: Synthetic

<400> SEQUENCE: 3
acacgacgct cttccgatct ccgagtgaca tg                              32

<210> SEQ ID NO 4
<211> LENGTH: 32
<212> TYPE: DNA
<213> ORGANISM: Artificial Sequence
<220> FEATURE:
<223> OTHER INFORMATION: Synthetic

<400> SEQUENCE: 4
acacgacgct cttccgatct cgtactgtca tg                              32

<210> SEQ ID NO 5
<211> LENGTH: 32
<212> TYPE: DNA
<213> ORGANISM: Artificial Sequence
<220> FEATURE:
<223> OTHER INFORMATION: Synthetic

<400> SEQUENCE: 5
acacgacgct cttccgatct atgtgctaca tg                              32

<210> SEQ ID NO 6
<211> LENGTH: 32
<212> TYPE: DNA
<213> ORGANISM: Artificial Sequence
<220> FEATURE:
<223> OTHER INFORMATION: Synthetic

<400> SEQUENCE: 6
acacgacgct cttccgatct ggtctcacca tg                              32

<210> SEQ ID NO 7
<211> LENGTH: 31
<212> TYPE: DNA
<213> ORGANISM: Artificial Sequence
<220> FEATURE:
<223> OTHER INFORMATION: Synthetic

<400> SEQUENCE: 7
```
acacgacgct cttccgatct agactcgcat g                                      31

<210> SEQ ID NO 8
<211> LENGTH: 32
<212> TYPE: DNA
<213> ORGANISM: Artificial Sequence
<220> FEATURE:
<223> OTHER INFORMATION: Synthetic

<400> SEQUENCE: 8
acacgacgct cttccgatct atactcgcca tg                                     32

<210> SEQ ID NO 9
<211> LENGTH: 31
<212> TYPE: DNA
<213> ORGANISM: Artificial Sequence
<220> FEATURE:
<223> OTHER INFORMATION: Synthetic

<400> SEQUENCE: 9
acacgacgct cttccgatct atgagaccat g                                      31

<210> SEQ ID NO 10
<211> LENGTH: 32
<212> TYPE: DNA
<213> ORGANISM: Artificial Sequence
<220> FEATURE:
<223> OTHER INFORMATION: Synthetic

<400> SEQUENCE: 10
acacgacgct cttccgatct actcgataca tg                                     32

<210> SEQ ID NO 11
<211> LENGTH: 32
<212> TYPE: DNA
<213> ORGANISM: Artificial Sequence
<220> FEATURE:
<223> OTHER INFORMATION: Synthetic

<400> SEQUENCE: 11
acacgacgct cttccgatct gctagtagca tg                                     32

<210> SEQ ID NO 12
<211> LENGTH: 32
<212> TYPE: DNA
<213> ORGANISM: Artificial Sequence
<220> FEATURE:
<223> OTHER INFORMATION: Synthetic

<400> SEQUENCE: 12
acacgacgct cttccgatct ctgcgagtca tg                                     32

<210> SEQ ID NO 13
<211> LENGTH: 32
<212> TYPE: DNA
<213> ORGANISM: Artificial Sequence
<220> FEATURE:
<223> OTHER INFORMATION: Synthetic

<400> SEQUENCE: 13
acacgacgct cttccgatct ggctactgca tg                                     32

<210> SEQ ID NO 14
<211> LENGTH: 32
<212> TYPE: DNA
<213> ORGANISM: Artificial Sequence

```
<220> FEATURE:
<223> OTHER INFORMATION: Synthetic

<400> SEQUENCE: 14
acacgacgct cttccgatct acgcatgtca tg                                32

<210> SEQ ID NO 15
<211> LENGTH: 32
<212> TYPE: DNA
<213> ORGANISM: Artificial Sequence
<220> FEATURE:
<223> OTHER INFORMATION: Synthetic

<400> SEQUENCE: 15
acacgacgct cttccgatct catctactca tg                                32

<210> SEQ ID NO 16
<211> LENGTH: 32
<212> TYPE: DNA
<213> ORGANISM: Artificial Sequence
<220> FEATURE:
<223> OTHER INFORMATION: Synthetic

<400> SEQUENCE: 16
acacgacgct cttccgatct gagacacaca tg                                32

<210> SEQ ID NO 17
<211> LENGTH: 32
<212> TYPE: DNA
<213> ORGANISM: Artificial Sequence
<220> FEATURE:
<223> OTHER INFORMATION: Synthetic

<400> SEQUENCE: 17
acacgacgct cttccgatct cagcgtacca tg                                32

<210> SEQ ID NO 18
<211> LENGTH: 32
<212> TYPE: DNA
<213> ORGANISM: Artificial Sequence
<220> FEATURE:
<223> OTHER INFORMATION: Synthetic

<400> SEQUENCE: 18
acacgacgct cttccgatct gctctacaca tg                                32

<210> SEQ ID NO 19
<211> LENGTH: 32
<212> TYPE: DNA
<213> ORGANISM: Artificial Sequence
<220> FEATURE:
<223> OTHER INFORMATION: Synthetic

<400> SEQUENCE: 19
acacgacgct cttccgatct cctgcataca tg                                32

<210> SEQ ID NO 20
<211> LENGTH: 32
<212> TYPE: DNA
<213> ORGANISM: Artificial Sequence
<220> FEATURE:
<223> OTHER INFORMATION: Synthetic

<400> SEQUENCE: 20
acacgacgct cttccgatct acactgatca tg                                32
```

```
<210> SEQ ID NO 21
<211> LENGTH: 32
<212> TYPE: DNA
<213> ORGANISM: Artificial Sequence
<220> FEATURE:
<223> OTHER INFORMATION: Synthetic

<400> SEQUENCE: 21
acacgacgct cttccgatct catagctgca tg                              32

<210> SEQ ID NO 22
<211> LENGTH: 31
<212> TYPE: DNA
<213> ORGANISM: Artificial Sequence
<220> FEATURE:
<223> OTHER INFORMATION: Synthetic

<400> SEQUENCE: 22
acacgacgct cttccgatct cgtactacat g                               31

<210> SEQ ID NO 23
<211> LENGTH: 32
<212> TYPE: DNA
<213> ORGANISM: Artificial Sequence
<220> FEATURE:
<223> OTHER INFORMATION: Synthetic

<400> SEQUENCE: 23
acacgacgct cttccgatct gatatgtgca tg                              32

<210> SEQ ID NO 24
<211> LENGTH: 16
<212> TYPE: DNA
<213> ORGANISM: Artificial Sequence
<220> FEATURE:
<223> OTHER INFORMATION: Synthetic

<400> SEQUENCE: 24
gatctgaaga gctcgt                                                16

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
acgagctctt ccgatctgtt                                            20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
acacgacgct cttccgatct                                            20

<210> SEQ ID NO 27
<211> LENGTH: 58
<212> TYPE: DNA
<213> ORGANISM: Artificial Sequence
<220> FEATURE:
<223> OTHER INFORMATION: Synthetic
```

<400> SEQUENCE: 27
aatgatacgg cgaccaccga gatctacact ctttccctac acgacgctct tccgatct    58

<210> SEQ ID NO 28
<211> LENGTH: 36
<212> TYPE: DNA
<213> ORGANISM: Artificial Sequence
<220> FEATURE:
<223> OTHER INFORMATION: Synthetic

<400> SEQUENCE: 28
caagcagaag acggcatacg agctcttccg atctgt    36

<210> SEQ ID NO 29
<211> LENGTH: 15
<212> TYPE: DNA
<213> ORGANISM: Artificial Sequence
<220> FEATURE:
<223> OTHER INFORMATION: Synthetic

<400> SEQUENCE: 29
gatcggaaga gctcg    15

<210> SEQ ID NO 30
<211> LENGTH: 19
<212> TYPE: DNA
<213> ORGANISM: Artificial Sequence
<220> FEATURE:
<223> OTHER INFORMATION: Synthetic

<400> SEQUENCE: 30
gatctagcct tctcgagca    19

<210> SEQ ID NO 31
<211> LENGTH: 58
<212> TYPE: DNA
<213> ORGANISM: Artificial Sequence
<220> FEATURE:
<223> OTHER INFORMATION: Synthetic

<400> SEQUENCE: 31
aatgatacgg cgaccaccga gatctacact ctttccctac acgacgctct tccgatct    58

<210> SEQ ID NO 32
<211> LENGTH: 36
<212> TYPE: DNA
<213> ORGANISM: Artificial Sequence
<220> FEATURE:
<223> OTHER INFORMATION: Synthetic

<400> SEQUENCE: 32
caagcagaag acggcatacg agctcttccg atctag    36

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
acacgacgct cttccgatct    20

<210> SEQ ID NO 34

```
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(28)
<223> OTHER INFORMATION: n is a, c, g, or t

<400> SEQUENCE: 34
acacgacgct cttccgatct nnnnnnnnca tgy                                  33

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
aacagatctg aagagctcgt                                                 20

<210> SEQ ID NO 36
<211> LENGTH: 19
<212> TYPE: DNA
<213> ORGANISM: Artificial Sequence
<220> FEATURE:
<223> OTHER INFORMATION: Synthetic

<400> SEQUENCE: 36
acgagctctt ccgatctgt                                                  19

<210> SEQ ID NO 37
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(28)
<223> OTHER INFORMATION: n is a, c, g, or t

<400> SEQUENCE: 37
acacgacgct cttccgatct nnnnnnnnca tgy                                  33

<210> SEQ ID NO 38
<211> LENGTH: 16
<212> TYPE: DNA
<213> ORGANISM: Artificial Sequence
<220> FEATURE:
<223> OTHER INFORMATION: Synthetic

<400> SEQUENCE: 38
gatcggaaga gctcgt                                                     16

<210> SEQ ID NO 39
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(28)
<223> OTHER INFORMATION: n is a, c, g, or t

<400> SEQUENCE: 39
```

```
acacgacgct cttccgatct nnnnnnnnca tgy                              33
```

<210> SEQ ID NO 40
<211> LENGTH: 16
<212> TYPE: DNA
<213> ORGANISM: Artificial Sequence
<220> FEATURE:
<223> OTHER INFORMATION: Synthetic

<400> SEQUENCE: 40

```
gatcggaaga gctcgt                                                 16
```

<210> SEQ ID NO 41
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(13)
<223> OTHER INFORMATION: n is a, c, g, or t

<400> SEQUENCE: 41

```
rcatgnnnnn nnnagatcgg aagagcgtcg tgt                              33
```

GENOTYPING BY NEXT-GENERATION SEQUENCING

This application is a continuation of U.S. patent application Ser. No. 13/739,874, filed Jan. 11, 2013, which claims priority to U.S. provisional patent application 61/586,596, filed Jan. 13, 2012, each of which is incorporated herein by reference in its entirety.

STATEMENT REGARDING FEDERALLY SPONSORED RESEARCH OR DEVELOPMENT

This invention was made with government support under Grant Numbers IOS-1027527, IOS-0820610, IOS-0910642, and DEB0919348 awarded by the National Science Foundation. The government has certain rights in the invention.

FIELD OF INVENTION

Provided herein is technology relating to genotyping and particularly, but not exclusively, to methods for genotyping one or more subjects by genome sequencing.

BACKGROUND

Next-generation sequencing enables researchers to obtain large amounts of data at a reduced cost and thus provides a tremendous opportunity to genotype an individual of any species in depth (Lai et al. "Genome-wide patterns of genetic variation among elite maize inbred lines" 2010, *Nat Genet* 42: 1027-1030). Recently, several genotyping-by-sequencing (GBS) approaches were developed to genotype hundreds of individuals simultaneously (Andolfatto et al. "Multiplexed shotgun genotyping for rapid and efficient genetic mapping" 2011, *Genome Res* 21: 610-17; Baird et al. "Rapid SNP discovery and genetic mapping using sequenced RAD markers" 2008, *PLoS One* 3: e3376; Elshire et al. "A Robust, Simple Genotyping-by-Sequencing (GBS) Approach for High Diversity Species" 2011 *PLoS One* 6: e19379).

Conventional genotyping is most often conducted using pre-defined SNP markers that must be discovered and validated in advance; these markers are often population-specific. These SNPs are typically detected via hybridization or by individual SNP-specific PCR-based assays. In contrast, GBS technology enables the detection of a wider range of polymorphisms than PCR-based assays (e.g., SNPs plus small insertions and/or deletions, e.g., "indels"). GBS technology eliminates the need to pre-discover and validate polymorphisms. Hence, GBS can be used in any polymorphic species and any segregating population.

However, conventional GBS methods share at least two drawbacks. First, conventional methods use double-stranded adaptors and, consequently, associated methods require stringent control of the template:adaptor concentration ratio in the adaptor ligation. As a result, precisely quantified, high quality input DNA is required as a starting material (see, e.g., Elshire et al.). Second, these methods survey hundreds of thousands or more sites and thus require numerous sequencing reads to generate enough coverage for each site in each sample.

SUMMARY

Accordingly, provided herein are technologies related to GBS. In particular, embodiments of the technology are provided that use a single-stranded oligonucleotide in lieu of the conventional double-stranded adaptors for the ligation reaction (see, e.g., Liu. et al. "DLA-based strategies for cloning insertion mutants: cloning the gl4 locus of maize using Mu transposon tagged alleles" 2009 *Genetics* 183: 1215-25, incorporated herein by reference in its entirety for all purposes). For example, a single-stranded oligonucleotide is less subject to self-ligation as a double-stranded adaptor is and thus the template:adaptor ratio is much less critical than in conventional approaches.

Furthermore, in some embodiments of the technology, a method of single-stranded oligonucleotide digestion and ligation is used to "barcode" or index a nucleic acid (e.g., a DNA). Consequently, in some embodiments, numerous (e.g., hundreds, thousands, tens of thousands, millions, etc.) barcoded DNAs are combined into a single multiplexed sample for analysis while maintaining source information in the barcode for each DNA. After analysis, the data are deconvoluted to obtain the data relevant to each barcoded DNA.

In some embodiments of the technology, two restriction enzymes are used to generate two sites with different overhangs at each end of the digested fragments. One site is ligated with the barcode oligonucleotide to permit multiplexing of samples during analysis, e.g., sequencing. The other site is ligated with an oligonucleotide without the barcode. The number of sites targeted for analysis (e.g., by sequencing) is further reduced by the design and selection of amplification primers complementary to the non-barcode site. By manipulating the choice of restriction enzymes and barcode sequences embodiments of the GBS technology provided herein are "tunable" in that a researcher is able to assay genotypes at a pre-defined number of genetic markers and multiplex the genotyping of the desired number of individuals. For example, in some embodiments of the technology, hundreds of markers are assayed per individual, while in other embodiments thousands or even tens of thousands of markers are assayed per individual. If fewer markers are assayed, then less sequencing is needed per individual. Consequently, costs are reduced by multiplexing multiple samples in one experiment and genotyping more individuals per unit of cost.

In some embodiments, a restriction enzyme is used that generates a fragment having an overhang that is ligated with a barcode oligonucleotide. The barcode oligonucleotide comprises a sequence complementary to the overhang, the DNA barcode, and a common sequence used as, e.g., a primer binding site for amplification. Using different barcodes allows the pooling of DNAs from different sources and the subsequent deconvolution of data for each individual subject providing a DNA. For a given sequence target of interest, a single primer is designed to bind to a region neighboring the enzyme recognition site at the target. This single primer, combined with a second primer complementary to the common sequence of the barcode oligonucleotide, is used for amplification, e.g., by PCR. In some embodiments, multiple primers are designed in accord with the desired number of targets and assigned to a primer plex. In these embodiments, multiple targets are amplified in a pool of barcoded DNAs.

The technology finds use, e.g., to genotype a population with hundreds to thousands of individual subjects even in the absence of prior genotyping information. The ability to tune the GBS technology provides researchers with a unique flexibility to apply GBS to a wide variety of projects, e.g., in the seed and livestock breeding industries, for protection of intellectual property, in the field of forensics, and for paternity testing in both humans and livestock. This list is intended to be exemplary and not limiting of the applications suitable for the technology provided. Moreover, some embodiments comprise target enrichment methods (e.g., sequence capture) to sequence targeted regions on a large number of individuals. Additional embodiments and applications will be apparent to persons skilled in the relevant art based on the teachings contained herein.

Accordingly, provided herein are embodiments of methods comprising digesting a nucleic acid with a restriction enzyme to produce a fragment; ligating a single-stranded barcode oligonucleotide to the fragment to produce a template; amplifying the template to produce an amplicon; and sequencing the amplicon to produce a sequence read. In some embodiments, a template pool is produced by mixing a plurality of templates, e.g., in some embodiments, a template pool is produced by mixing a plurality of templates from a plurality of individuals. Some embodiments further provide parsing the sequence read, mapping the sequence read, and assigning a genotype. In some embodiments of the methods, the nucleic acid is digested with two different restriction enzymes, e.g., NspI and BfuCI. Some embodiments provide that the single-stranded barcode oligonucleotide identifies a subject that was the source of the nucleic acid. Some embodiments provide that the amplifying comprises the use of a target specific primer, e.g., to select an amplicon for sequencing.

As such, the technology described provides a method for genotyping by sequencing, the method comprising providing a first plurality of nucleic acids from a first subject; providing a second plurality of nucleic acids from a second subject; digesting the first plurality of nucleic acids with a restriction enzyme to produce a first plurality of fragments; digesting the second plurality of nucleic acids with the restriction enzyme to produce a second plurality of fragments; ligating a first single-stranded barcode oligonucleotide to each fragment of the first plurality of fragments to produce a first plurality of templates; ligating a second single-stranded barcode oligonucleotide to each fragment of the second plurality of fragments to produce a second plurality of templates; mixing the first plurality of templates and the second plurality of templates to produce a template pool; amplifying a subset of the template pool using a target specific primer to produce a plurality of amplicons; sequencing the plurality of amplicons to produce a plurality of sequence reads; and deconvoluting the sequence reads using a first sequence of the first barcode oligonucleotide and a second sequence of the second barcode oligonucleotide.

Moreover, associated with the technology are embodiments of compositions comprising a single-stranded barcode oligonucleotide, wherein the single-stranded barcode oligonucleotide comprises a sequence selected from the group consisting of SEQ ID NOs: 1-23. In some embodiments, the compositions further comprise a second single-stranded oligonucleotide. In some embodiments, a composition is provided comprising a nucleic acid, wherein the nucleic acid sequence comprises a sequence of a single-stranded barcode oligonucleotide, a sequence of a target site, and a sequence of a second single-stranded oligonucleotide. Some embodiments of the compositions further comprise a first amplification primer complementary to the single-stranded barcode oligonucleotide and a target specific amplification primer complementary to the second single-stranded oligonucleotide.

Moreover, the technology provides embodiments of a use of a composition described above for genotyping one or more subjects and embodiments of a kit comprising a composition described above.

BRIEF DESCRIPTION OF THE DRAWINGS

These and other features, aspects, and advantages of the present technology will become better understood with regard to the following drawings:

FIG. 1 is a drawing describing a method embodiment of the technology provided herein.

FIG. 2 is a drawing describing a method embodiment of the technology provided herein.

FIG. 3 is a drawing describing a method embodiment of the technology provided herein.

DETAILED DESCRIPTION

Figure 4:
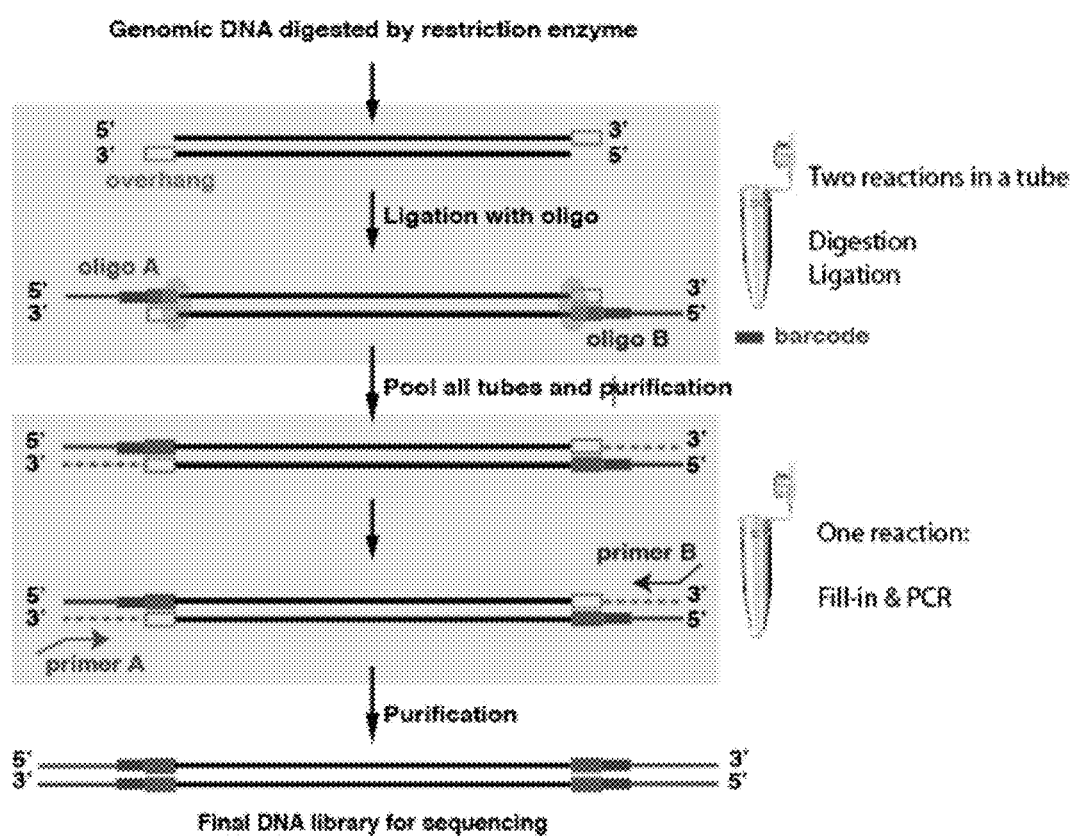
FIG. 4 is a drawing describing a method embodiment of the technology provided herein.

Provided herein is technology relating to genotyping and particularly, but not exclusively, to methods for genotyping one or more subjects by genome sequencing. Is some embodiments, the technology uses single-stranded barcode oligonucleotides and target selection to tune the sequencing.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The term "subject" refers to a biological organism such as a human or other animal (e.g., a pig, a cow, a mouse, etc.) and the like, or a plant, bacterium, archaon, or virus. In some embodiments, any entity having a genotype is a subject.

The term "gene" refers to a nucleic acid (e.g., DNA or RNA) sequence that comprises coding sequences necessary for the production of an RNA or a polypeptide or its precursor. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "heterologous" when used in reference to a gene refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise gene sequences that comprise cDNA forms of a gene; the cDNA sequences may be expressed in either a sense (to produce mRNA) or anti-sense orientation (to produce an anti-sense RNA transcript that is complementary to the mRNA transcript). Heterologous genes are distinguished from endogenous genes in that the heterologous gene sequences are typically joined to nucleotide sequences comprising regulatory elements such as promoters that are not found naturally associated with the gene for the protein encoded by the heterologous gene or with gene sequences in the chromosome, or are associated with portions of the chromosome not found in nature (e.g., genes expressed in loci where the gene is not normally expressed).

As used herein, the phrase "dNTP" means deoxynucleotidetriphosphate, where the nucleotide is any nucleotide, such as A, T, C, G or U.

As used herein, a "nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art. The term should be understood to include, as equivalents, analogs of either DNA or RNA made from nucleotide analogs. The term as used herein also encompasses cDNA, that is complementary, or copy, DNA produced from an RNA template, for example by the action of reverse transcriptase.

The term "nucleotide sequence of interest" or "nucleic acid sequence of interest" refers to any nucleotide sequence (e.g., RNA or DNA), the manipulation of which may be deemed desirable for any reason (e.g., for analysis, for quantification, to treat disease, confer improved qualities, etc.) by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The terms "oligonucleotide" or "polynucleotide" or "nucleotide" or "nucleic acid" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. When present in a DNA form, the oligonucleotide may be single-stranded (i.e., the sense strand) or double-stranded.

The terms "complementary" and "complementarity" refer to polynucleotides (e.g., a sequence of nucleotides) related by the base-pairing rules. For example, for the sequence 5'-A-G-T-3' is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is frequently that gene which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, an "allele" refers to an alternative sequence at a particular locus; the length of an allele can be as small as 1 nucleotide base, but is typically larger. Allelic sequence can be amino acid sequence or nucleic acid sequence.

As used herein, a "locus" is a short sequence that is usually unique and usually found at one particular location in the genome by a point of reference; e.g., a short DNA sequence that is a gene, or part of a gene or intergenic region. In some embodiments, a locus is a unique PCR product at a particular location in the genome. Loci may comprise one or more polymorphisms; i.e., alternative alleles present in some individuals.

Thus, the terms "variant" and "mutant" when used in reference to a nucleotide sequence refer to an nucleic acid sequence that differs by one or more nucleotides from another, usually related nucleotide acid sequence. A "variation" is a difference between two different nucleotide sequences; typically, one sequence is a reference sequence.

As used herein, "marker" means a polymorphic nucleic acid sequence or nucleic acid feature. In a broader aspect, a "marker" can be a detectable characteristic that can be used to discriminate between heritable differences between organisms. Examples of such characteristics may include genetic markers, protein composition, protein levels, oil composition, oil levels, carbohydrate composition, carbohydrate levels, fatty acid composition, fatty acid levels, amino acid composition, amino acid levels, biopolymers, pharmaceuticals, starch composition, starch levels, fermentable starch, fermentation yield, fermentation efficiency, energy yield, secondary compounds, metabolites, morphological characteristics, and agronomic characteristics.

As used herein, "polymorphism" means the presence of one or more variations of a nucleic acid sequence at one or more loci in a population of one or more individuals. The variation may comprise but is not limited to one or more base changes, the insertion of one or more nucleotides or the deletion of one or more nucleotides. A polymorphism includes a single nucleotide polymorphism (SNP), a simple sequence repeat (SSR) and indels, which are insertions and deletions. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the later may be associated with rare but important phenotypic variation. In some embodiments, a "polymorphism" is a variation among individuals in sequence, particularly in DNA sequence, or feature, such as a transcriptional profile or methylation pattern. Useful polymorphisms include single nucleotide polymorphisms (SNPs), insertions or deletions in DNA sequence (indels), simple sequence repeats of DNA sequence (SSRs) a restriction fragment length polymorphism, a haplotype, and a tag SNP. A genetic marker, a gene, a DNA-derived sequence, a RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern may comprise polymorphisms.

The term "polymorphic locus" refers to a genetic locus present in a population that shows variation between members of the population.

The term "detection assay" refers to an assay for detecting the presence or absence of a wild-type or variant nucleic acid sequence (e.g., mutation or polymorphism) in a given allele of a particular gene, or for detecting the presence or absence of a particular protein or the activity or effect of a particular protein or for detecting the presence or absence of a variant of a particular protein.

As used herein, "typing" refers to any method whereby the specific allelic form of a given corn genomic polymorphism is determined. For example, a single nucleotide polymorphism (SNP) is typed by determining which nucleotide is present (e.g., an A, G, T, or C). Insertion/deletions (indels) are determined by determining if the indel is present. Indels can be typed by a variety of assays including, but not limited to, marker assays.

As used herein, the term "single nucleotide polymorphism," also referred to by the abbreviation "SNP," means a polymorphism at a single site wherein the polymorphism constitutes a single base pair change, an insertion of one or more base pairs, or a deletion of one or more base pairs.

As used herein, "genotype" means the genetic component of the phenotype and it can be indirectly characterized using markers or directly characterized by nucleic acid sequencing. Suitable markers include a phenotypic character, a metabolic profile, a genetic marker, or some other type of marker. A genotype may constitute an allele for at least one genetic marker locus or a haplotype for at least one haplotype window. In some embodiments, a genotype may represent a single locus and in others it may represent a genome-wide set of loci. In another embodiment, the genotype can reflect the sequence of a portion of a chromosome, an entire chromosome, a portion of the genome, and the entire genome.

As used herein, "phenotype" means the detectable characteristics of a cell or organism which are a manifestation of gene expression.

As used herein, "barcode" shall generally mean a virtual or a known nucleotide sequence that is used as an index for labeling a DNA fragment and/or a library and for constructing a multiplex library. A library includes, but is not limited to, a genomic DNA library, a cDNA library, and a ChIP library. A plurality of DNAs, each of which is separately labeled with a distinct barcode, may be pooled together to form a multiplex barcoded library for performing sequencing simultaneously, in which each barcode is sequenced together with its flanking tags located in the same construct and thereby serves as a index for the DNA fragment and/or library labeled by it. In some embodiments, a barcode is made with a specific nucleotide sequence having 1, 2, 3, 4, 5, 6, or more nucleotides in length. The length of a barcode may be increased along with the maximum sequencing length of a sequencer. The terms "barcoded adaptor" and "barcoded adaptor sequence" are interchangeable. The terms "barcode" and "barcode sequence" are interchangeable.

As used herein, "virtual" shall generally mean not in actual form but existing or resulting in effect.

As used herein, "index" shall generally mean a distinctive or identifying mark or characteristic.

As used herein, "restriction enzyme recognition site" and "restriction enzyme binding site" are interchangeable.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

The term "primer" refers to an oligonucleotide, whether occurring naturally as in a purified restriction digest or produced synthetically, that is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

One with ordinary skill in the art of design of primers will recognize that a given primer need not hybridize with 100% complementarity to prime the synthesis of a complementary nucleic acid strand. Primer pair sequences may be a "best fit" amongst several aligned sequences, thus they need not be fully complementary to the hybridization region of any one of the sequences in the alignment. Moreover, a primer may hybridize over one or more segments such that intervening or adjacent segments are not involved in the hybridization event (e.g., for example, a loop structure or a hairpin structure). The primers may comprise at least 70%, at least 75%, at least 80%, at least 85%, at least 90%, at least 95% or at least 99% sequence identity with a target nucleic acid of interest. Thus, in some embodiments, an extent of variation of 70% to 100%, or any range falling within, of the sequence identity is possible relative to the specific primer sequences disclosed herein. To illustrate, determination of sequence identity is described in the following example: a primer 20 nucleobases in length which is identical to another 20 nucleobase primer having two non-identical residues has 18 of 20 identical residues (18/20=0.9 or 90% sequence identity). In another example, a primer 15 nucleobases in length having all residues identical to a 15 nucleobase segment of primer 20 nucleobases in length would have 15/20=0.75 or 75% sequence identity with the 20 nucleobase primer. Percent identity need not be a whole number, for example when a 28 consecutive nucleobase primer is completely identical to a 31 consecutive nucleobase primer (28/31=0.9032 or 90.3% identical).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some embodiments, complementarity of primers with respect to the conserved priming regions of viral nucleic acid, is between about 70% and about 80%. In other embodiments, homology, sequence identity or complementarity, is between about 80% and about 90%. In yet other embodiments, homology, sequence identity or complementarity, is at least 90%, at least 92%, at least 94%, at least 95%, at least 96%, at least 97%, at least 98%, at least 99% or is 100%.

In some embodiments, the primers described herein comprise at least 70%, at least 75%, at least 80%, at least 85%, at least 90%, at least 92%, at least 94%, at least 95%, at least 96%, at least 98%, or at least 99%, or 100% (or any range falling within) sequence identity with the primer sequences specifically disclosed herein.

In some embodiments, any given primer comprises a modification comprising the addition of a non-templated T residue to the 5' end of the primer (i.e., the added T residue does not necessarily hybridize to the nucleic acid being amplified). The addition of a non-templated T residue has an effect of minimizing the addition of non-templated A residues as a result of the non-specific enzyme activity of, e.g., Taq DNA polymerase (Magnuson et al., Biotechniques, 1996: 21, 700-709), an occurrence which may lead to ambiguous results arising from molecular mass analysis.

Primers may contain one or more universal bases. Because any variation (due to codon wobble in the third position) in the conserved regions among species is likely to occur in the third position of a DNA (or RNA) triplet, oligonucleotide primers can be designed such that the nucleotide corresponding to this position is a base which can bind to more than one nucleotide, referred to herein as a "universal nucleobase." For example, under this "wobble" base pairing, inosine (I) binds to U, C or A; guanine (G) binds to U or C, and uridine (U) binds to U or C. Other examples of universal nucleobases include nitroindoles such as 5-nitroindole or 3-nitropyrrole (Loakes et al., Nucleosides and Nucleotides, 1995, 14, 1001-1003), the degenerate nucleotides dP or dK, an acyclic nucleoside analog containing 5-nitroindazole (Van Aerschot et al., Nucleosides and Nucleotides., 1995, 14, 1053-1056) or the purine analog 1-(2-deoxy-beta-D-ribofuranosyl)-imidazole-4-carboxamide (Sala et al., Nucl. Acids Res., 1996, 24, 3302-3306).

In some embodiments, to compensate for weaker binding by the wobble base, oligonucleotide primers are configured such that the first and second positions of each triplet are occupied by nucleotide analogs that bind with greater affinity than the unmodified nucleotide. Examples of these analogs include, but are not limited to, 2,6-diaminopurine which binds to thymine, 5-propynyluracil which binds to adenine and 5-propynylcytosine and phenoxazines, including G-clamp, which binds to G. Propynylated pyrimidines are described in U.S. Pat. Nos. 5,645,985, 5,830,653 and 5,484,908, incorporated herein by reference in their entireties. Propynylated primers are described in U.S. Pat. Appl. Pub. No. 2003-0170682, incorporated herein by reference in its entirety. Phenoxazines are described in U.S. Pat. Nos. 5,502,177, 5,763,588, and 6,005,096, each of which is incorporated herein by reference in its entirety. G-clamps are described in U.S. Pat. Nos. 6,007,992 and 6,028,183, each of which is incorporated herein by reference in its entirety.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences, that are removed from their natural environment, isolated or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence refers broadly to any composition containing the given polynucleotide sequence. The composition may comprise an aqueous solution, e.g., containing salts (e.g., NaCl), detergents (e.g., SDS), and other components.

The term "sample" is used in its broadest sense. In one sense it can refer to an animal cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

Embodiments of the Technology

In one aspect, the technology provides methods for genotyping-by-sequencing. For example, in some embodiments, a plurality of DNAs is sequenced at one or more loci, markers, SNPs, or other sites of interest. The methods provide that DNA is digested with a restriction enzyme, e.g., a sample comprising 10 ng, 100 ng, 1000 ng, etc. of genomic DNA (in some embodiments, RNase treated DNA) is digested with one or more restriction enzymes, e.g., NspI and/or BfuCI, in an appropriate buffer (e.g., a commercially available buffer (e.g., as supplied by NEB)) under appropriate conditions for digestion. After digestion the digested fragments are ligated to a single-stranded barcoded (indexed) oligonucleotide, e.g., as provided in Table 1. In some embodiments, a second oligonucleotide, e.g., as provided in Table 2, is ligated to the other end of the digested fragments.

TABLE 1

Barcode oligonucleotide sequences

| name | sequence | SEQ NO: ID |
|---|---|---|
| nspl1 | 5' ACACGACGCTCTTCCGATCTCGTATATGCATG 3' | 1 |
| nspl2 | 5' ACACGACGCTCTTCCGATCTCACGCTACATG 3' | 2 |
| nspl3 | 5' ACACGACGCTCTTCCGATCTCCGAGTGACATG 3' | 3 |
| nspl4 | 5' ACACGACGCTCTTCCGATCTCGTACTGTCATG 3' | 4 |
| nspl5 | 5' ACACGACGCTCTTCCGATCTATGTGCTACATG 3' | 5 |
| nspl6 | 5' ACACGACGCTCTTCCGATCTGGTCTCACCATG 3' | 6 |
| nspl7 | 5' ACACGACGCTCTTCCGATCTAGACTCGCATG 3' | 7 |
| nspl8 | 5' ACACGACGCTCTTCCGATCTATACTCGCCATG 3' | 8 |
| nspl9 | 5' ACACGACGCTCTTCCGATCTATGAGACCATG 3' | 9 |

TABLE 1-continued

Barcode oligonucleotide sequences

| name | sequence | SEQ NO: ID |
|---|---|---|
| nspl10 | 5' ACACGACGCTCTTCCGATCTACTCGATACATG 3' | 10 |
| nspl12 | 5' ACACGACGCTCTTCCGATCTGCTAGTAGCATG 3' | 11 |
| nspl13 | 5' ACACGACGCTCTTCCGATCTCTGCGAGTCATG 3' | 12 |
| nspl14 | 5' ACACGACGCTCTTCCGATCTGGCTACTGCATG 3' | 13 |
| nspl15 | 5' ACACGACGCTCTTCCGATCTACGCATGTCATG 3' | 14 |
| nspl16 | 5' ACACGACGCTCTTCCGATCTCATCTACTCATG 3' | 15 |
| nspl18 | 5' ACACGACGCTCTTCCGATCTGAGACACACATG 3' | 16 |
| nspl19 | 5' ACACGACGCTCTTCCGATCTCAGCGTACCATG 3' | 17 |
| nspl21 | 5' ACACGACGCTCTTCCGATCTGCTCTACACATG 3' | 18 |
| nspl22 | 5' ACACGACGCTCTTCCGATCTCCTGCATACATG 3' | 19 |
| nspl23 | 5' ACACGACGCTCTTCCGATCTACACTGATCATG 3' | 20 |
| nspl97 | 5' ACACGACGCTCTTCCGATCTCATAGCTGCATG 3' | 21 |
| nspl99 | 5' ACACGACGCTCTTCCGATCTCGTACTACATG 3' | 22 |
| nspl100 | 5' ACACGACGCTCTTCCGATCTGATATGTGCATG 3' | 23 |

The barcode oligonucleotide comprises a sequence common to every barcode oligonucleotide, a barcode sequence that is unique to every barcode oligonucleotide, and a sequence that is complementary to the single-stranded end produced by the restriction enzyme. In some embodiments, the second oligonucleotide comprises a sequence that is complementary to a single-stranded end produced by the second restriction enzyme or, in some embodiments, to a sequence near or adjacent to a target site of interest (e.g., a marker, SNP, allele, locus, polymorphic site, etc.). In some embodiments the barcode oligonucleotide comprises a phosphorothioate linkage, e.g., after the 5' A in the sequences provided in Table 1.

TABLE 2

Second (non-barcode) oligonucleotide sequences

| name | 5' sequence 3' | SEQ ID NO: |
|---|---|---|
| bfuci12mm | 5' GATCTGAAGAGCTCGT 3' | 24 |
| s-SEO15 | 5' P-GATCGGAAGAGCTC*G 3' | 29 |

An asterisk (*) denotes a phosphorothioate bond and a P- denotes 5'-phosphorylation In some embodiments, multiple ligated samples (e.g., from multiple subjects, samples, sources, BACs, etc.) are mixed to provide a pooled sample. In some embodiments, the samples are purified to remove contaminants or components from previous reactions (e.g., salts, enzymes) that may inhibit subsequent steps of the methods. In some embodiments, the purification is performed using a commercial kit, e.g., the Qiaquick PCR purification kit (Qiagen, Cat#28106 or Cat#28104). In some embodiments, the sample is size-selected, e.g., to enrich the sample for fragments greater than 250 bp in size, e.g., using AMPure beads (Agencourt, Beckman Coulter).

In some embodiments, DNAs in the pooled sample comprise multiple markers, SNPs, loci, target sites, BACs, etc.

Accordingly, in some embodiments an amplification (e.g., PCR) using one or more target selection primers in combination with a common primer selects one or more target sites for further analysis (e.g., by specifically enriching target sites in the sample DNAs). Amplification primers comprise a phosphorothioate bond in some embodiments.

In some embodiments, nucleic acid molecules are analyzed and characterized by any of a wide variety of methods, including, but not limited to, sequencing, hybridization analysis, amplification (e.g., via polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA)).

Finally, in some embodiments, the sample is subjected to another amplification to produce a sample suitable for sequencing, e.g., by using primer 1.1 and final3 as shown in Table 3. Amplification primers comprise a phosphorothioate bond in some embodiments.

TABLE 3 amplification oligonucleotides

| name | sequence (5' to 3') | SEQ ID NO: |
|---|---|---|
| bfuci3ACAA | ACGAGCTCTTCCGATCTGTT | 25 |
| common | ACACGACGCTCTTCCGATCT | 26 |
| s-common1 | A*CACGACGCTCTTCCGATC*T | 33 |
| s-SE016CTA | G*A*T*CTAGCCTTCTCGAGCA | 30 |
| primer 1.1 | AATGATACGGCGACCACCGAGATCTACACTCT TTCCCTACACGACGCTCTTCCGATCT | 27 |
| final3 | CAAGCAGAAGACGGCATACGAGCTCTTCCGAT CTGT | 28 |
| s-SE-P1 | A*ATGATACGGCGACCACCGAGATCTACACTC TTTCCCTACACGACGCTCTTCCGATC*T | 31 |
| s-SE-P2AG | C*AAGCAGAAGACGGCATACGAGCTCTTCCGA TCTA*G | 32 |

An asterisk (*) denotes a phosphorothioate bond

In some embodiments, the technology employs a sequencing technology. In some aspects, DNA sequencing methodologies associated with the present technology comprise Second Generation (a.k.a. Next Generation or Next-Gen), Third Generation (a.k.a. Next-Next-Gen), or Fourth Generation (a.k.a. N3-Gen) sequencing technologies including, but not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the present technology provides parallel sequencing of partitioned amplicons (PCT Publication No: WO2006084132 to Kevin McKernan et al., herein incorporated by reference in its entirety). In some embodiments, DNA sequencing is achieved by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. No. 6,787,308; U.S. Pat. No. 6,833,246; herein incorporated by reference in their entireties), the Lynx massively parallel signature sequencing technology (Brenner et al. (2000). Nat. Biotechnol. 18:630-634; U.S. Pat. No. 5,695,934; U.S. Pat. No. 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbial.*, 7:287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., *Clinical Chem.*, 55: 641-658, 2009; MacLean et al., *Nature Rev. Microbial.*, 7: 287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7:287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., *Clinical Chem.*, 55:641-658, 2009; MacLean et al., *Nature Rev. Microbial.*, 7:287-296; U.S. Pat. No. 5,912,148; U.S. Pat. No. 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing is employed (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, HeliScope by Helicos BioSciences is employed (Voelkerding et al., *Clinical Chem.*, 55: 641-658, 2009; MacLean et al., *Nature Rev. Microbiol.*, 7:287-296; U.S. Pat. No. 7,169,560; U.S. Pat. No. 7,282,337; U.S. Pat. No. 7,482,120; U.S. Pat. No. 7,501,245; U.S. Pat. No. 6,818,395; U.S. Pat. No. 6,911,345; U.S. Pat. No. 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., *Science* 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs. However, the cost of acquiring a pH-mediated sequencer is approximately $50,000, excluding sample preparation equipment and a server for data analysis.

Another exemplary nucleic acid sequencing approach that may be adapted for use with the present invention was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "HIGH THROUGHPUT NUCLEIC ACID SEQUENCING BY EXPANSION," filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. No. 11/671,956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectable fluorescence resonance energy transfer (FRET) upon nucleotide addition.

Another real-time single molecule sequencing system developed by Pacific Biosciences (Voelkerding et al., *Clinical Chem.*, 55: 641-658, 2009; MacLean et al., *Nature Rev. Microbiol.*, 7:287-296; U.S. Pat. No. 7,170,050; U.S. Pat. No. 7,302,146; U.S. Pat. No. 7,313,308; U.S. Pat. No. 7,476,503; all of which are herein incorporated by reference) utilizes reaction wells 50-100 nm in diameter and encompassing a reaction volume of approximately 20 zeptoliters ($10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high, biologically relevant concentrations, the detection volume is occupied by nucleotides only a small fraction of the time. In addition, visits to the detection volume are fast, lasting only a few microseconds, due to the very small distance that diffusion has to carry the nucleotides. The result is a very low background.

Processes and systems for such real time sequencing that may be adapted for use with the invention are described in, for example, U.S. Pat. No. 7,405,281, entitled "Fluorescent nucleotide analogs and uses therefor", issued Jul. 29, 2008 to Xu et al.; U.S. Pat. No. 7,315,019, entitled "Arrays of optical confinements and uses thereof", issued Jan. 1, 2008 to Turner et al.; U.S. Pat. No. 7,313,308, entitled "Optical analysis of molecules", issued Dec. 25, 2007 to Turner et al.; U.S. Pat. No. 7,302,146, entitled "Apparatus and method for analysis of molecules", issued Nov. 27, 2007 to Turner et al.; and U.S. Pat. No. 7,170,050, entitled "Apparatus and methods for optical analysis of molecules", issued Jan. 30, 2007 to Turner et al.; and U.S. Pat. Pub. Nos. 20080212960, entitled "Methods and systems for simultaneous real-time monitoring of optical signals from multiple sources", filed Oct. 26, 2007 by Lundquist et al.; 20080206764, entitled "Flowcell system for single molecule detection", filed Oct. 26, 2007 by Williams et al.; 20080199932, entitled "Active surface coupled polymerases", filed Oct. 26, 2007 by Hanzel et al.; 20080199874, entitled "CONTROLLABLE STRAND SCISSION OF MINI CIRCLE DNA", filed Feb. 11, 2008 by Otto et al.; 20080176769, entitled "Articles having localized molecules disposed thereon and methods of producing same", filed Oct. 26, 2007 by Rank et al.; 20080176316, entitled "Mitigation of photodamage in analytical reactions", filed Oct. 31, 2007 by Eid et al.; 20080176241, entitled "Mitigation of photodamage in analytical reactions", filed Oct. 31, 2007 by Eid et al.; 20080165346, entitled "Methods and systems for simultaneous real-time monitoring of optical signals from multiple sources", filed Oct. 26, 2007 by Lundquist et al.; 20080160531, entitled "Uniform surfaces for hybrid material substrates and methods for making and using same", filed Oct. 31, 2007 by Korlach; 20080157005, entitled "Methods and systems for simultaneous real-time monitoring of optical signals from multiple sources", filed Oct. 26, 2007 by Lundquist et al.; 20080153100, entitled "Articles having localized molecules disposed thereon and methods of producing same", filed Oct. 31, 2007 by Rank et al.; 20080153095, entitled "CHARGE SWITCH NUCLEOTIDES", filed Oct. 26, 2007 by Williams et al.; 20080152281, entitled "Substrates, systems and methods for analyzing materials", filed Oct. 31, 2007 by Lundquist et al.; 20080152280, entitled "Substrates, systems and methods for analyzing materials", filed Oct. 31, 2007 by Lundquist et al.; 20080145278, entitled "Uniform surfaces for hybrid material substrates and methods for making and using same", filed Oct. 31, 2007 by Korlach; 20080128627, entitled "SUBSTRATES, SYSTEMS AND METHODS FOR ANALYZING MATERIALS", filed Aug. 31, 2007 by Lundquist et al.; 20080108082, entitled "Polymerase enzymes and reagents for enhanced nucleic acid sequencing", filed Oct. 22, 2007 by Rank et al.; 20080095488, entitled "SUBSTRATES FOR PERFORMING ANALYTICAL REACTIONS", filed Jun. 11, 2007 by Foquet et al.; 20080080059, entitled "MODULAR OPTICAL COMPONENTS AND SYSTEMS INCORPORATING SAME", filed Sep. 27, 2007 by Dixon et al.; 20080050747, entitled "Articles having localized molecules disposed thereon and methods of producing and using same", filed Aug. 14, 2007 by Korlach et al.; 20080032301, entitled "Articles having localized molecules disposed thereon and methods of producing same", filed Mar. 29, 2007 by Rank et al.; 20080030628, entitled "Methods and systems for simultaneous real-time monitoring of optical signals from multiple sources", filed Feb. 9, 2007 by Lundquist et al.; 20080009007, entitled "CONTROLLED INITIATION OF PRIMER EXTENSION", filed Jun. 15, 2007 by Lyle et al.; 20070238679, entitled "Articles having localized molecules disposed thereon and methods of producing same", filed Mar. 30, 2006 by Rank et al.; 20070231804, entitled "Methods, systems and compositions for monitoring enzyme activity and applications thereof", filed Mar. 31, 2006 by Korlach et al.; 20070206187, entitled "Methods and systems for simultaneous real-time monitoring of optical signals from multiple sources", filed Feb. 9, 2007 by Lundquist et al.; 20070196846, entitled "Polymerases for nucleotide analogue incorporation", filed Dec. 21, 2006 by Hanzel et al.; 20070188750, entitled "Methods and systems for simultaneous real-time monitoring of optical signals from multiple sources", filed Jul. 7, 2006 by Lundquist et al.; 20070161017, entitled "MITIGATION OF PHOTODAMAGE IN ANALYTICAL REACTIONS", filed Dec. 1, 2006 by Eid et al.; 20070141598, entitled "Nucleotide Compositions and Uses Thereof", filed Nov. 3, 2006 by Turner et al.; 20070134128, entitled "Uniform surfaces for hybrid material substrate and methods for making and using same", filed Nov. 27, 2006 by Korlach; 20070128133, entitled "Mitigation of photodamage in analytical reactions", filed Dec. 2, 2005 by Eid et al.; 20070077564, entitled "Reactive surfaces, substrates and methods of producing same", filed Sep. 30, 2005 by Roitman et al.; 20070072196, entitled "Fluorescent nucleotide analogs and uses therefore", filed Sep. 29, 2005 by Xu et al; and 20070036511, entitled "Methods and systems for monitoring multiple optical signals from a single source", filed Aug. 11, 2005 by Lundquist et al.; and Korlach et al. (2008) "Selective aluminum passivation for targeted immobilization of single DNA polymerase molecules in zero-mode waveguide nanostructures" PNAS 105(4): 1176-81, all of which are herein incorporated by reference in their entireties.

Subsequently, in some embodiments, the data produced comprises sequence data from multiple barcoded DNAs. Using the known association between the barcode and the source of the DNA, the data can be deconvoluted to assign sequences to the source subjects, samples, organisms, etc. The sequences are mapped, in some embodiments, to a reference DNA sequence (e.g., a chromosome) and genotypes are assigned to the source subjects, samples, organisms, etc., e.g., by modeling, e.g., by a Hidden Markov Model.

Some embodiments provide a processor, data storage, data transfer, and software comprising instructions to assign genotypes. Some embodiments of the technology provided herein further comprise functionalities for collecting, storing, and/or analyzing data. For example, some embodiments comprise the use of a processor, a memory, and/or a database for, e.g., storing and executing instructions, analyzing data, performing calculations using the data, transforming the data, and storing the data. In some embodiments, the processor is configured to calculate a function of data derived from the sequences and/or genotypes determined. In some embodiments, the processor performs instructions in software configured for medical or clinical results reporting and in some embodiments the processor performs instructions in software to support non-clinical results reporting.

Many genotyping tests involve determining the presence or absence, or measuring the amount of, multiple genotypes, and an equation comprising variables representing the properties of multiple genotypes produces a value that finds use in making a diagnosis or assessing the presence or qualities of a genotype. As such, in some embodiments the software calculates this value and, in some embodiments, presents the value to the user, uses the value to produce an indicator related to the result (e.g., an LED, an icon on an LCD, a sound, or the like), stores the value, transmits the value, or uses the value for additional calculations.

In some embodiments, the processor is used to initiate and/or terminate the sequencing and data collection. In some embodiments, a device or system is provided comprising a user interface (e.g., a keyboard, buttons, dials, switches, and the like) for receiving user input that is used by the processor to determine one or more genotypes. In some embodiments, the device further comprises a data output for transmitting (e.g., by a wired or wireless connection) data to an external destination, e.g., a computer, a display, a network, and/or an external storage medium.

Different applications require different numbers of markers. Accordingly, the technology finds use, for example, in genotyping large populations wherein one may which to provide "tunable" numbers of genetic markers, e.g., in breeding applications (backcrossing, identification of QTL, association mapping) as well as for the protection of IP (elite varieties) and paternity testing and forensics. In addition, embodiments of the methods find use in efficiently adding a separate DNA barcode (an index) to each of multiple samples to provide a high degree of multiplexing. The technology finds use in experiments involving multiple pooled environmental samples, e.g., to identify the organisms present in multiple environments (e.g., guts from multiple humans, different water samples, etc). The technology is useful for the quality control of biological samples (e.g., cell lines) prior to conducting expensive experiments on such samples.

In addition, the barcoding provided relates to genome sequencing. Traditionally genomes were sequenced BAC-by-BAC using Sanger technology. This approach can provide high quality assemblies for complex genomes. More recently genomes have been sequenced using a "whole genome shotgun" (WGS) approach enabled by next generation sequencing (NGS) technologies. This approach is substantially cheaper than the traditional BAC-based ordered approach, but at the cost of assembly quality. The technology provided herein finds use in combining the resolution of BAC-by-BAC sequencing with the efficiency of NGS. For example, individual BACs are digested and bar-coded using the technology (e.g., as embodied by the exemplary methods below) and then pooled for sequencing. Post-sequencing, each BAC is assembled individually. Overlaps among BACs are identified via sequence comparisons, thus eliminating the need to generate a "minimum tiling path" of BACs. Sequence gaps within BACs are filled using WGS data.

Although the disclosure herein refers to certain illustrated embodiments, it is to be understood that these embodiments are presented by way of example and not by way of limitation.

EXAMPLES

Method 1—Tunable GBS

Next-generation sequencing enables researchers to obtain large amounts of data at a reduced cost and thus provides a tremendous opportunity to genotype an individual in depth. Provided herein is a method of restriction enzyme digestion followed by single stranded oligonucleotide ligation to barcode (e.g., index) the sources of DNAs. Two restriction enzymes are used that generate two sites with different overhangs at each end of each digested fragment. One site is ligated with the "barcode" oligonucleotide to permit multiplexing of samples during sequencing. The other site is ligated with the oligonucleotide without the "barcode". The number of targeted sites is further reduced through the primer selection on the non-barcode site during the amplification procedure. See FIGS. 1 and 3.

1. Digestion
100-200 ng genomic DNA (RNase treated)
3 µl 10×NEB Buffer 4
3 µl 10×BSA
0.8 µl NspI
1 µl BfuCI
sterile H$_2$O to 30 µl
Incubate at 37° C. for 1.5 hour
2. Ligation
After 1.5 hours incubation, add 30 µl ligation solution to genomic DNA digestion reaction:
1.5-2.0 µl barcode oligo (e.g., from nspIxx or Nxx series) (50-100 µM)
1.5-2.0 µl non-barcode oligo (e.g., bfuci12 mm, s-SEO15, etc.) (50-100 µM)
3 µl 10× ligase buffer
1-1.5 µl T4 DNA ligase
sterile water to 30 µl
Total volume per reaction is now 60 µl. Incubate for 1.5 hours at 20° C. and then at 80° C. for 20 minutes to inactivate the enzyme.
3. Purification
1) Pool all ligated samples (each 60 µl) and completely mix them evenly
2) Aliquot 1.5 ml for purification, e.g., in two Qiagen columns
3) Follow the manufacturer's instructions to purify the ligation products (eg. as provided by Qiagen, Catalog numbers 28106 or 28104).
4) Elute DNA in 100 µl EB buffer
4. Size selection
1) Add AMPure beads to the eluted DNA according to the manufacturer's instructions and vortex to mix
2) Incubate for 5-20 minutes at ambient temperature
3) Using a magnetic particle concentrator (MPC), pellet the beads against the wall of the tube.
4) Remove the supernatant and wash the beads twice with 100-500 µl of 70% ethanol, incubating for 30 seconds each time
5) Remove all the supernatant and allow the AMPure beads to air dry completely
6) Remove the tube from the MPC, add 24-50 µl of EB, and vortex to resuspend the beads
7) Using the MPC, pellet the beads against the wall of the tube once more and transfer the supernatant containing the purified nebulized DNA to a new microcentrifuge tube
5. Selective PCR amplification
1) PCR mixture:
2-15 µl purified ligated DNA (approximately 100-200 ng DNA)
25 µl 2× Phusion High-Fidelity PCR Master Mix
1 µl selective primer (e.g., bfuci3ACAA, s-SEO16CTA, s-SEO16ACA) (100 µM)
1 µl common primer (e.g., common1, s-common1) (100 µM)
sterile water to 50 µl
2) Run PCR, e.g., using the PCR program: 98° C. for 30 minutes; 15 cycles of 98° C. for 10 seconds, 62° C. for 30 seconds, 72° C. for 30 seconds; and a final extension at 72° C. for 5 minutes.
3) PCR purification according to the protocol in the QIAquick PCR purification kit; elute with 50 µl of EB.
6. Final PCR amplification
1) PCR Mixture:
5-10 µl purified selected PCR product
25 µl 2× Phusion High-Fidelity PCR Master Mix
1 µl first primer (e.g., Primer 1.1, s-SE-P1, etc.) (100 µM)
1 µl second primer (e.g., final3, s-SE-P2AG, s-SE-P2GT) (100 µM)
sterile water to 50 µl
The primers for the final PCR are designed to match binding site sequences determined by the primers used in the selective PCR, e.g., s-SE-P2AG is used in the Final PCR if s-SEO16CTA was used in the selective PCR and s-SE-P2GT is used in the Final PCR if s-SEO16ACA was used in the selective PCR
2) Run PCR, e.g., using the PCR program of 98° C. for 30 minutes; 15 cycles of 98° C. for 10 seconds, 65° C. for 30 seconds, 72° C. for 30 seconds; and a final extension at 72° for 5 minutes.
3) PCR purification, e.g., according to the protocol in the QIAquick PCR purification kit; elute with 30 µl of EB.
4) Measure the concentration of purified products, e.g., by nanodrop. Yield of PCR should be ≥1.0 µg
5) Run Bioanalyzer DNA 1000 for size and concentration confirmation.
The sample is now ready for sequencing, data collection, and genotyping.

Method 2—Single Primer Genotyping

Provided herein is an embodiment of the technology as a method in which restriction enzyme digestion is followed by single-stranded oligo ligation to barcode (e.g., index) the sources of DNAs. A restriction enzyme generates an overhang at one end of each digested fragment. A "barcoded" oligonucleotide comprising a common sequence is ligated to the digested DNAs. After ligation, the many sources of DNAs with different barcoded oligonucleotides are pooled. A single primer is designed on a polymorphic target. In combination with the primer matching the common sequence in the barcoded oligo, this single primer is used to amplify the target site. Primers of multiple target sites can be plexed for amplification. See FIGS. 2 and 4.
Most steps below are best performed in sterile microfuge tubes:
1. Digestion
100-200 ng genomic DNA (RNase treated)
3 µl 10×NEB Buffer 4
3 µl 10×BSA
0.8-1.2 µl restriction enzyme, e.g., NspI or BanII
Sterile, nuclease free H$_2$O to 30 µl
Incubate at 37° C. for 1.5 hour
2. Ligation
After the 1.5-hour incubation, add 20 µl of ligation solution to genomic DNA digestion reaction:
1.5-2 µl barcode oligo (100 µM)
2-3 µl 10× ligase buffer
1-1.5 µl T4 DNA ligase
sterile water to 20-22 µl
Total volume per reaction is now 50 µl. Incubate for 1.5 hours at 20° C. and then at 65° C. for 20 minutes to inactivate the enzyme. Pool all ligated samples equally and completely mix them evenly.
The barcode oligo may be a single oligo or a mixture of two (or more) oligos (e.g., a oligo of the nspIxx, Nxx series).
3. Target PCR amplification
1) PCR mixture:
2-12 µl purified ligated DNA (approximately 100-200 ng DNA)
25 µl 2× Phusion High-Fidelity PCR Master Mix
2 µl common primer (5 µM)
1.5 µl multiple target specific primers (5 µM each)
sterile water to 50 µl 2) Run PCR using the program; 98° C. for 30 minutes; 12 cycles of 98° C. for 10 seconds, 62° C. for 30 seconds, 72° C. for 30 seconds; and a final extension at 72° C. for 5 minutes.
3) PCR purification according to the protocol in the QIAquick PCR purification kit; elute with 50 μl of EB.
4. Final PCR amplification
1) PCR mixture:
2 μl 10× diluted target PCR product
25 μl 2× Phusion High-Fidelity PCR Master Mix
1 μl Illumina PCR Primer 1
1 μl Illumina PCR Primer 2
sterile water to 50 μl
2) Run PCR using the PCR program consists of 98° C. for 30 minutes; 20 cycles of 98° C. for 10 seconds, 65° C. for 30 seconds, 72° C. for 30 seconds; and a final extension at 72° C. for 5 minutes.
3) PCR purification according to the protocol in the QIAquick PCR purification kit; elute with 30 μl of EB.
4) Measure the concentration of purified products by nanodrop. Yield of PCR should be ≥1.0 μg
5) Run Bioanalyzer DNA 1000 for size and concentration confirmation.
The sample is now ready for sequencing, data collection, and genotyping.
In some embodiments of single primer genotyping, methods are provided as follows:
1. Digestion
Nuclease-free water to 30 μl
DNA (RNase treated) 100-200 ng
10×NEB Buffer 4 3 μl
10×BSA 3 μl
Restriction enzyme, e.g., NspI or BanII 1 μl
Total 30 μl
Incubate at 37° C. for 1.5 hours
2. Ligation
After 1.5 hour-incubation, add 30 μl ligation solution to the genomic DNA digestion reaction:
Nuclease-free water 22 μl
Left oligo (50 μM) 2 μl
Right oligo (50 μM) 2 μl
10× ligase buffer 3 μl
T4 ligase 1 μl
Total 30 μl
Total volume per reaction is now 60 μl. Incubate for 1.5 hours at 16° C. and 80° C. for 20 minutes to inactivate the enzyme.
3. Purification
Pool all ligated samples (each 60 μl) and completely mix them
Aliquot 1 ml for further purification (e.g., in a Qiagen column); the remaining mixture may be retained (e.g., stored at −20° C.)
Purify ligation products by suitable means, e.g., by Qiaquick PCR purification kit
Elute DNA (e.g., in 100 μl EB buffer) in each tube
Measure the concentration, e.g., by Nanodrop 4. PCR amplification
1) PCR mixture
Molecular grade water 13 μl
Purified ligated DNA 10 μl (~200 ng)
2× Phusion Master Mix 25 μl
First primer (e.g., s-SE-P1) 20 μM, M 1 μl
Second primer (e.g., TruSeq-final-primer) 20 μM, M 1 μl
Total 50 μl
2) Thermocycle
5. AMpure Size Selection (>100 bp DNA Enriched, 1.2:1 Ratio)
Add 120 μl of AMPure beads to the 100 μl eluted DNA.
Vortex briefly to mix
Incubate for 15 min at ambient temperature
Using a Magnetic Particle Concentrator (MPC), pellet the beads against the wall of the tube.
Remove the supernatant and wash the beads twice with 200 μl of 70% ethanol, incubating for 30 seconds each time
Remove the supernatant and allow the AMPure beads to air dry (~5-10 minutes)
Remove the tube from the MPC, add 50 μl of EB, and vortex to resuspend the beads
Using the MPC, pellet the beads against the wall of the tube once more and transfer the supernatant containing the purified nebulized DNA to a new microcentrifuge tube
6. Measure the concentration of purified products by nanodrop.
7. Run Bioanalyzer DNA Chip for size and concentration confirmation.
8. Optional cloning of final DNA library for the confirmation Example 1

During the development of embodiments of the technology described herein, experiments were conducted to verify the methods provided. A sample was prepared to assess the tunable GBS method against 956 previously called B73 versus Mo17 SNPs. Samples were prepared according to the methods provided, taking a total time of approximately one day. The methods produced 19 samples for analysis and the sequencing yielded 37 million 100-bp reads, or, alternatively, approximately 2 million reads per sample. An average of 5000 SNPs were called per sample and 820 SNPs with genotyping calls for at least 12 of the 19 samples were produced. This resulted in a genotyping accuracy of approximately 99%.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in relevant fields are intended to be within the scope of the following claims.

We claim:

1. A method for genotyping-by-sequencing a sample, the method comprising:
   1) providing a first fully single-stranded oligonucleotide comprising a first primer binding site and a second fully single-stranded oligonucleotide comprising a second primer binding site;
   2) ligating said first fully single-stranded oligonucleotide to the first ends of nucleic acid fragments produced by digesting nucleic acids from the sample with a restriction enzyme and ligating said second fully single-stranded oligonucleotide to the second ends of the nucleic acid fragments to produce a plurality of templates comprising single-stranded ends;
   3) amplifying said templates using a first amplification primer that hybridizes to the first primer binding site or complement thereof and a second amplification primer that hybridizes to the second primer binding site or complement thereof to produce amplicons;
   4) acquiring sequence reads from the amplicons; and
   5) genotyping-by-sequencing the sample by determining a genotype of the sample using one or more sequence reads, wherein:
   a) said first amplification primer comprises a 5' portion and a 3' portion, wherein:
      1) said 5' portion of said first amplification primer hybridizes to said first primer binding site or complement thereof; and
      2) said 3' portion of said first amplification primer hybridizes to one or more bases of nucleic acid fragments, said bases being adjacent to the first primer binding site in a subset of the plurality of templates; and/or
   b) said second amplification primer comprises a 5' portion and a 3' portion, wherein:
      1) said 5' portion of the second amplification primer hybridizes to said second primer binding site or complement thereof; and
      2) said 3' portion of said second amplification primer hybridizes to one or more bases of nucleic acid fragments, said bases being adjacent to the second primer binding site in a subset of the plurality of templates.

2. The method of claim 1 further comprising mapping one or more sequence reads to a reference sequence.

3. The method of claim 1 wherein the nucleic acids from the sample are digested with two different restriction enzymes.

4. The method of claim 1 wherein the first fully single-stranded oligonucleotide and/or the second fully single-stranded oligonucleotide comprises a common sequence, a unique sequence, and a sequence complementary to the single-stranded end produced by the restriction enzyme.

5. The method of claim 1 further comprising assembling a plurality of overlapping sequence reads.

6. The method of claim 1 wherein the first amplification primer comprises:
   a) a 5' portion that hybridizes to the first primer binding site or complement thereof; and
   b) a 3' portion comprising 1-3 nucleotides, said 3' portion hybridizing to a subset of the plurality of templates.

7. The method of claim 1 further comprising synthesizing or providing an amplification primer comprising a 5' portion adjacent to a 3' portion, the 5' portion comprising a sequence that hybridizes to the first primer binding site or complement thereof and the 3' portion comprising 1 to 10 nucleotides appended to the 3' end of the 5' portion of the amplification primer.

8. The method of claim 1 wherein the first single-stranded oligonucleotide comprises a barcode and/or the second oligonucleotide comprises a barcode.

9. The method of claim 8 wherein the barcode of the first single-stranded oligonucleotide and/or the barcode of the second oligonucleotide identifies a subject and/or a sample that was the source of the nucleic acid.

10. The method of claim 1 wherein the first single-stranded oligonucleotide and the second oligonucleotide comprise the same nucleotide sequence.

11. The method of claim 1 wherein the first single-stranded oligonucleotide and the second oligonucleotide comprise different nucleotide sequences.

12. The method of claim 1 wherein the 3' portion of the first amplification primer and/or the 3' portion of the second amplification primer comprises 1-10 nucleotides.

13. The method of claim 1 wherein the amplifying produces amplicons from a subset of the plurality of templates, wherein each template of the subset comprises a nucleic acid fragment that comprises a portion that hybridizes to the 3' portion of the first amplification primer and/or a portion that hybridizes to the 3' portion of the second amplification primer.

14. The method of claim 1 further comprising ligating a third fully single-stranded oligonucleotide comprising the first primer binding site to the first ends of second nucleic acid fragments produced by digesting nucleic acids from a second sample with the restriction enzyme and ligating the second fully single-stranded oligonucleotide to the second ends of the second nucleic acid fragments from the second sample to produce a second plurality of templates; mixing the second plurality of templates with the first plurality of templates; genotyping-by-sequencing the first sample by determining a genotype of the first sample using one or more sequence reads, and genotyping-by-sequencing the second sample by determining a genotype of the second sample using one or more sequence reads.

15. A method for genotyping-by-sequencing a plurality of samples, the method comprising:
1) providing a first fully single-stranded oligonucleotide comprising a primer binding site and a first distinct barcode, a second fully single-stranded oligonucleotide comprising said primer binding site and a second distinct barcode, and a fully single-stranded common oligonucleotide;
2) ligating said first fully single-stranded oligonucleotide to the first ends of first nucleic acid fragments produced by digesting nucleic acids from a first sample with a restriction enzyme and ligating said fully single-stranded common oligonucleotide to the second ends of the first nucleic acid fragments from the first sample to produce a first plurality of templates comprising single-stranded ends;
3) ligating said second fully single-stranded oligonucleotide to the first ends of second nucleic acid fragments produced by digesting nucleic acids from a second sample with the restriction enzyme and ligating said fully single-stranded common oligonucleotide to the second ends of the second nucleic acid fragments from the second sample to produce a second plurality of templates comprising single-stranded ends;
4) amplifying said templates from a template mixture comprising the first plurality of templates mixed with the second plurality of templates using a first amplification primer comprising a 5' portion that hybridizes to the primer binding site or complement thereof and a second amplification primer that hybridizes to the common oligonucleotide or complement thereof to produce amplicons, wherein said 5' portion of said first amplification primer hybridizes to said primer binding site or complement thereof and a 3' portion of said first amplification primer hybridizes to one or more bases of nucleic acid fragments, said bases being adjacent to the primer binding site in a subset of the plurality of templates;
5) acquiring sequence reads from the amplicons;
6) associating sequence reads comprising a sequence of the first barcode with the first sample and associating sequence reads comprising a sequence of the second barcode with the second sample; and
7) genotyping-by-sequencing the first sample by determining a genotype of the first sample using one or more sequence reads and genotyping-by-sequencing the second sample by determining a genotype of the second sample using one or more sequence reads.

16. The method of claim 15 wherein the first plurality of nucleic acids from the first sample are from a first subject and the second plurality of nucleic acids from the second sample are from a second subject.

* * * * *